US005620842A

United States Patent [19]
Davis et al.

[11] Patent Number: 5,620,842
[45] Date of Patent: Apr. 15, 1997

[54] DETERMINATION OF THE NUMBER OF FLUORESCENT MOLECULES ON CALIBRATION BEADS FOR FLOW CYTOMETRY

[75] Inventors: Kenneth A. Davis, Los Altos; James E. Bishop, Santa Cruz, both of Calif.

[73] Assignee: Becton Dickinson and Company, Franklin Lakes, N.J.

[21] Appl. No.: 413,045

[22] Filed: Mar. 29, 1995

[51] Int. Cl.[6] .................................................. G01N 31/00
[52] U.S. Cl. ............................. 435/4; 435/180; 435/967; 435/7.5; 436/528; 436/531; 436/10; 436/800
[58] Field of Search ................................ 435/967, 4, 7.5, 435/180; 436/528, 518, 524, 531, 8, 10, 800

[56] References Cited

U.S. PATENT DOCUMENTS

| | | | |
|---|---|---|---|
| 4,699,828 | 10/1987 | Schwart et al. | 428/402 |
| 5,380,663 | 1/1995 | Schwartz et al. | 436/10 |
| 5,478,722 | 12/1995 | Caldwell | 435/1.1 |
| 5,494,793 | 2/1996 | Schindele | 435/6 |

*Primary Examiner*—Marian C. Knode
*Assistant Examiner*—Rachel Heather Freed
*Attorney, Agent, or Firm*—Royal N. Ronning, Jr.

[57] ABSTRACT

A rapid, simple method for preparing beads for calibrating flow cytometers which contain a known number of fluorophores per bead is presented. Briefly, the invention utilizes beads coated with a stable complex of a fluorophore and an enzyme. the enzymatic activity of a known number of beads gives an accurate measure of fluorophore density on those beads.

14 Claims, 3 Drawing Sheets

DETERMINATION OF THE NUMBER OF FLUORESCENT MOLECULES ON CALIBRATION BEADS FOR FLOW CYTOMETRY

BACKGROUND OF INVENTION

Knowledge of the number of molecules of a particular antigen on a cell has been of increasing interest. This value is most often approximated on flow cytometry by measurement of the number of antibody molecules bound to that antigen on the cell. Such measurement requires that the flow cytometer to be calibrated.

Various approaches have been used to convert flow cytometric data of cell-bound antibody to the number of copies of antibody per cell. These include: radioactive antibody plus fluorescent second step; comparison to commercial calibration beads; and by analysis of binding curves from fluorescent antibody titrations. These different approaches have yielded variable copy numbers for antibodies bound to lymphocyte antigens. For example, reports of CD4 antibody vary from 46,000 to 132,000 copies per cell, CD8 antibody from 130,000 to 430,000 copies per cell, and CD45 antibody from 180,000 to 970,000 copies per cell. Further work on the basic methodology for broadly applicable standards was thus warranted.

A broadly applicable and intrinsically accurate standard would appear to be R-PE beads. Other approaches have certain drawbacks: 1) fluorescein is some 10-fold less bright than R-PE, self-quenches when molecules are brought into close proximity to each other, and therefore the number of fluoresceins conjugated per antibody molecule does not necessarily reflect fluorescence intensity; 2) the use of calibration beads with a known number of anti-mouse Ig binding sites is problematic due to different efficiencies of binding of different monoclonals, resulting in copy number determinations that vary by as much as 2-fold; 3) the use of radioactive antibody plus polyclonal fluorescein-labeled second step is problematic because the stoichiometry of second step to monoclonal varies with different monoclonals and may vary from lot to lot and depending upon the source of the polyclonal second step. In contrast, R-PE gives high sensitivity for low copy number antigens, R-PE beads alleviate the uncertainty in binding efficiency of antibody conjugates to anti-mouse beads, and R-PE conjugates are available as 1:1 conjugates thus giving a more straightforward relationship between R-PE copy number and antigen copy number. However, determining the amount of R-PE on a bead by direct fluorescence measurement suffers from the drawback that the presence of particles in suspension can interfere with that measurement.

SUMMARY OF INVENTION

The instant invention presents a rapid, simple method for preparing beads for calibrating flow cytometers which contain a known number of fluorophores per bead. Briefly, the invention utilizes beads coated with a stable complex of a fluorophore and an enzyme. The enzymatic activity of a known number of beads gives an accurate measure of fluorophore density on those beads.

In practice, a fluorophore is conjugated with biotin and an enzyme to form a biotin-fluorophore-enzyme conjugate. These conjugates will readily bind to the streptavidin coated beads to form a bead-streptavidin-biotin-fluorophore-enzyme complex. The specific enzymatic activity of the fluorophore-enzyme complex is known and, therefore, the amount of fluorophore attached to each bead can be determined by measuring the enzymatic activity of a known number of beads.

DETAILED DESCRIPTION OF THE INVENTION

Figure 1:
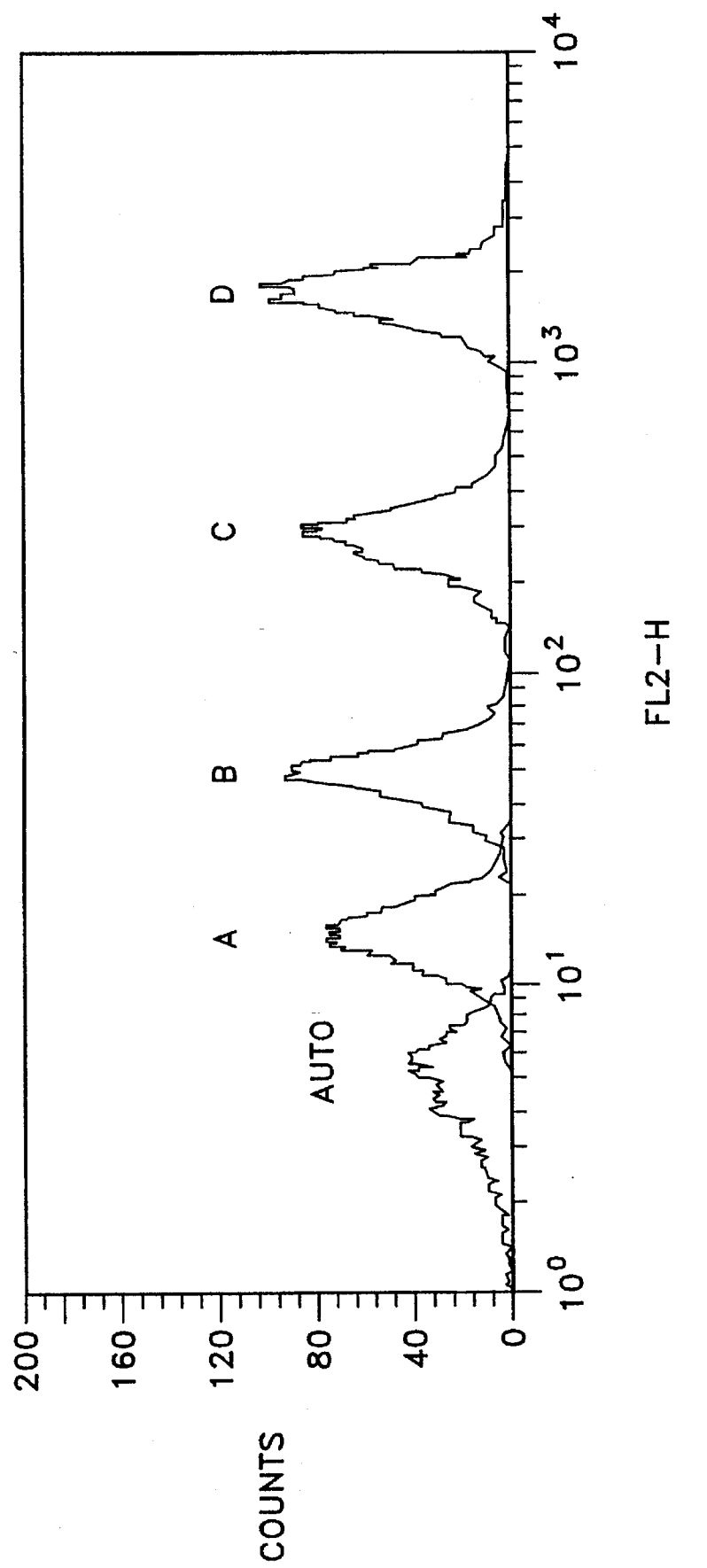
FIG. 1 presents flow cytometric evaluations of PE bead lots. PE bead lots A through E, plus the same bead with no PE, were read on a FACScan™ Lot E, the brightest, was off scale and not shown, but was estimated from readings at a lower FL2 PMT voltage to have a fluorescence of about 15,700.

The complexes of the instant invention are formed by complexation of the beads and the fluorophore/enzyme conjugates. This complexation is preferably performed by the use of a streptavidin/biotin linkage which facilitates the addition of variable amounts of fluorophore/enzyme conjugate per beads and the linkage nether greatly interferes with the activity of the fluorophore, nor of the enzyme. However, it is contemplated that the fluorophore can be conjugated to the bead by any of the methods which are known in the art, including, but not limited to, direct adsorption onto the bead surface and the use of other linking agents.

More specifically, biotinylated conjugates of fluorophore and enzyme are formed and the specific enzymatic activity (i.e., the activity of enzyme per unit of fluorophore) is determined experimentally. This value can then be used to determine the concentration of fluorophore in any mixture.

The ratio of fluorophore to enzyme must be kept constant to assure that enzymatic activity can be correlated with fluorophore concentration. In a preferred embodiment, this ratio is 1/1 (mole/mole). The fluorophore-enzyme complex in solution must accurately reflect the fluorophore-enzyme complex attached to beads.

The enzyme utilized can be any which can be conjugated to a fluorophore and which possesses a readily measurable activity. In a preferred embodiment, the enzyme used is alkaline phosphatase. The enzymatic assay for alkaline phosphatase can be any of the assays known to those in the art. In a preferred embodiment, the substrate is p-nitrophenylphosphate and the reaction is monitored spectrophotometrically at 405 nm.

The fluorophore utilized can similarly be any of the various fluorophores and/or fluorescent compounds (as used herein, the term fluorophore is inclusive of fluorophore and fluorescent compounds) known to be useful in flow cytometry, the primary criterion for use being the requirement that the optical property of the fluorophore not greatly interfere with the measurement of enzymatic activity. Preferably, the fluorophore is phycoerythrin(PE), but other useful fluorophores include APC, PerCP, and fluoresceinisothiocyanate (FITC).

The bead can similarly be any of those known to be useful in flow cytometry applications. The beads must be capable of forming a stable adduct of a fluorophore-enzyme complex. In a preferred embodiment, the bead is comprised of polymethylmethacrylate possessing amino functionalities on the surface. Biotin is attached to the amino groups and the beads are then admixed with streptavidin creating a streptavidin coated bead. It is to be understood, however, that other beads and/or surface functionalities can also be used. Subsequent addition of biotin-fluorophore-enzyme and free biotin or a biotinylated non-fluorescent, non-enzymatic protein in various proportions will create beads labelled with different levels of fluorophore-enzyme complex.

The beads, having a known number of fluorophore-enzyme complexes attached, can be used to calibrate flow cytometers for use in quantitative assays or to calibrate other beads with unknown concentrations of that fluorophore.

EXAMPLES

The following examples illustrate certain preferred embodiments of this invention, but are not intended to be illustrative of all embodiments.

1. MATERIALS.

R-Phycoerythrin (R-PE) (m.w. 240,000) was obtained from QuantaPhy, Inc. (Santa Cruz, Calif.) and the concentration determined using an extension coefficient of 8.3 $cm^{-1}$ $(mg/ml)^{-1}$.

R-PE was derivatized with biotin by standard means. The alkaline phosphatase (AP, calf intestine, Worthingto Biochemical Corp., Freehold N.J.) conjugate of R-PE-biotin (AP-PE-biotin) was made with heterobifunctional reagents SMCC and SPDP (Pierce Chemicals, Rockford, Ill.) by standard means. The crude reaction mixture was separated by size exclusion chromatography, and the 1:1 conjugate between AP and PE pooled. In order to preserve AP activity, the purified AP-PE-biotin was stored in a storage buffer consisting of: 50 mM Tris/1 mM $MgCl_2$/0.1 mM $ZnCl_2$/300 mM NaCl/0.1% $NaN_3$ pH 8.0 (Boehringer 1993) with 0.1% bovine serum albumin (BSA).

2. BEAD PREPARATION.

R-PE was also conjugated directly to streptavidin by the same method as biotin R-PE was conjugated to alkaline phosphatase.

Polymethylemthacrylate amino beads (5.7 microns, P(MMA/R-$NH_2$)Bangs Laboratories Inc. Carmel Ind.) in a 10% (w/v) suspension in PBS were washed with PBS containing 0.1% SDS, followed by PBS containing 0.01% Tween®20. The washed beads were then suspended to a 3% (w/v) concentration in PBS/Tween®20 and labeled with NHS-biotin by standard means.

Beads were admixed with mixtures of streptavidin-R-PE and unlabelled streptavidin in various proportions to give beads with varying levels of fluorophore per bead (FIG. 1).

Figure 2:
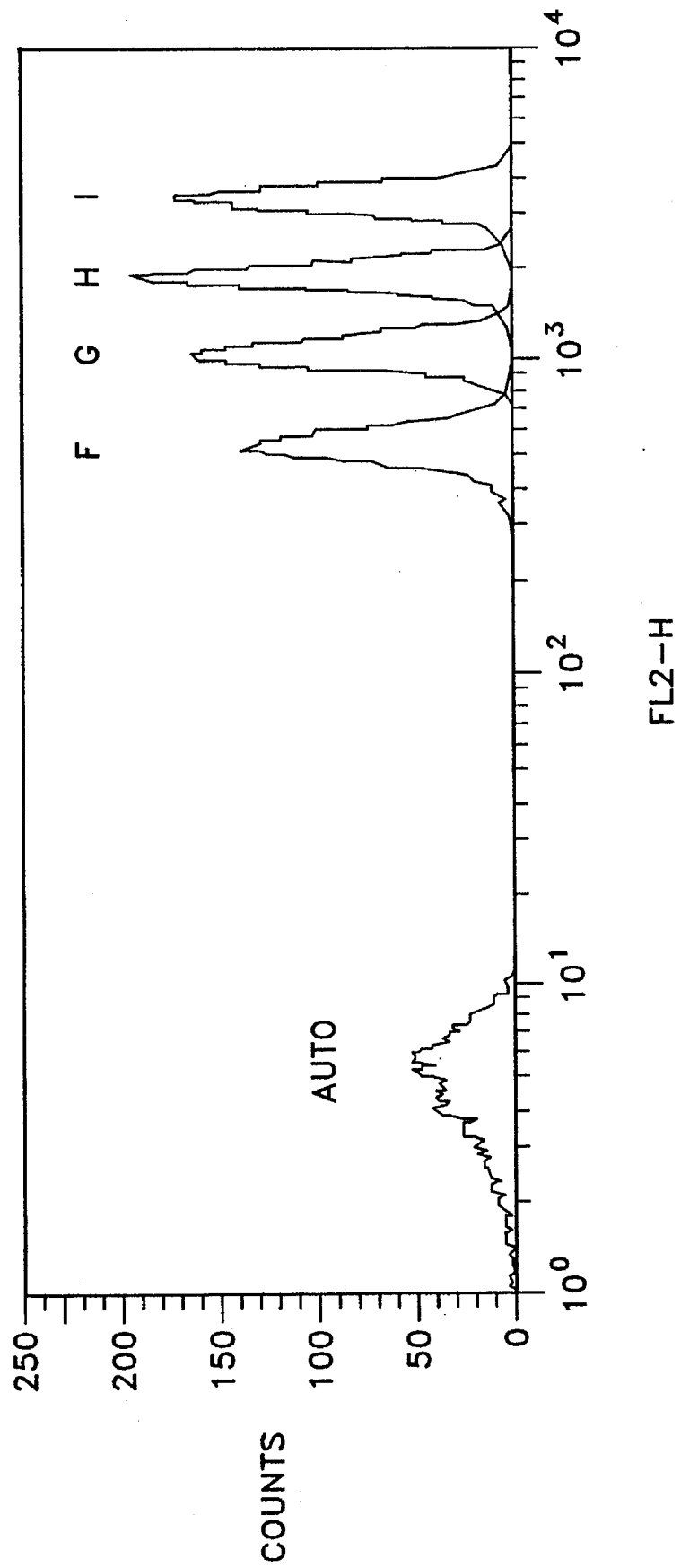
FIG. 2 presents flow cytometric evaluations of AP-PE-biotin bead lots. Bead lots F through I, made by staining streptavidin beads with different amounts of AP-PE-biotin, were read on a FACScan™ and compared with a negative (unstained) bead.

Other beads were admixed with a large excess of streptavidin (0.4 mg/ml) and incubated at room temperature for 2 hours to permit binding of streptavidin to the biotinylated beads. The coated beads were then washed and stored in PBS/0.1% $NAN_3$/0.5% BSA. Mixtures of AP-PE-biotin and free biotin in various proportions were added in excess to streptavidin coated beads to give beads containing varying levels of fluorophore-alkaline phosphatase complex per bead (FIG. 2). Beads were counted with a haemacytometer.

The enzymatic activity of AP-PE biotin in solution and preincubated with streptavidin beads was found to be the same, under conditions where approximately 50% of the AP-PE biotin was bound to the beads. Also, when streptavidin beads preincubated with AP-PE-biotin were sedimented by centrifugation, washed, and resuspended to the original volume, the enzymatic activity of the supernatant, plus the activity of the resuspended beads, equalled the starting activity. This indicates that the specific activity of the AP-PE-biotin complex is the same whether the complex is free or bound to beads.

3. FLUORESCENCE ANALYSIS FOR R-PE.

Flow Cytometry was performed using a FACScan™flow cytometer with CELL Quest™ software (Becton Dickinson, San Jose, Calif.).

R-PE fluorescence was measured in a Hitachi fluorimeter, model F-4010, with excitation at 500 nm, emission at 575 nm, and bandpasses for both of 20 nm. Additionally, a 500/20 nm excitation filter and an 0–56emission filter were used. The cuvette was standard 1 cm square with a volume of 3 ml. The full range of the fluorimeter extended from 0 to 2500 fluorescence units. Fluorescence of beads labeled with R-PE was corrected for predetermined levels of quenching (about 35% at bead concentrations of 25,000/microliter) compared to a standard curve of free R-PE. Five bead lots, each with different amounts of R-PE attached, were prepared. Their fluorescence values on a flow cytometer (except for the brightest off scale Lot E) are shown in FIG. 1. The total amount of PE and the bead concentration were used to calculate to the amount of PE per bead. The approximate values obtained for the five bead lots (Lot A through Lot E) in molecules of PE per bead were: 200, 780, 4300, 37300, and 187000.

4. ENZYMATIC ASSAY FOR R-PE.

Alkaline Phosphatase was measured in a Perkin Elmer spectrophotometer (model Lambda 2S) at 405 nm and 30° C. in a 1 cm path length cuvette in a buffer consisting of: 1× diethanolamine buffer, pH 9.8 (from 5× AP buffer; Pierce Chemicals); 0.5 mM MgCl2; 0.1% BSA; enzyme (as AP, AP-PE-biotin, or AP-PE-biotin beads); and 2 mM p-nitrophenyl phosphate (Sigma Chemicals, St. Louis, Mo.). Absorbance change was converted to moles using an extinction coefficient of 18.5 $mM^{-1}cm^{-1}$. Four lots of AP-PE-biotin beads (Lots F, G, H, and I) were prepared (FIG. 2) and were assayed for AP activity. PE concentration was estimated from a standard curve prepared from enzymatic analysis of free AP-PE-biotin. The number of PE molecules per bead were calculated from the PE concentration times Avagadro's number divided by the bead concentration. The resultant approximations of the number of PE molecules per bead for Lots F, G, H, and I were: 11,500; 19,000; 32,500; and 54,900.

Figure 3:
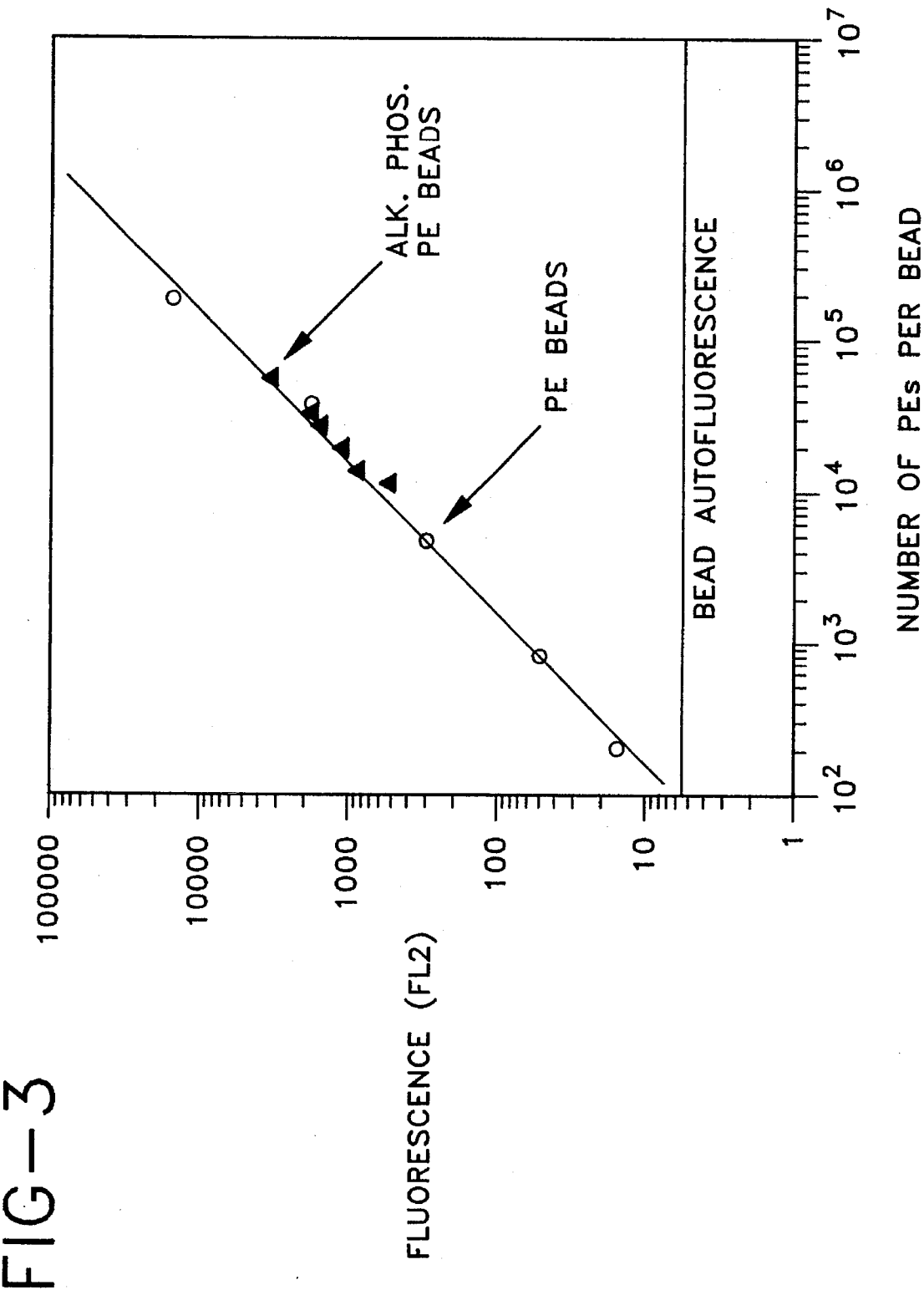
FIG. 3 presents comparisons of fluorescence by flow cytometry of PE on beads quantified by different methods. Concentration of R-PE on PE beads (Lots A–E, open circles), determined by direct fluorescence and on AP-PE-biotin beads (Lots F–I, solid triangles) determined from enzymatic activity. The fluorescence values determined by flow cytometryare plotted against the number of R-PE molecules per bead.

The results of the fluorescence determined by flow cytometry and the number of R-PE molecules determined by the two methods are compared in FIG. 3. The two methods are in good agreement and are relatively linear.

It is apparent that many modifications and variations of this invention as hereinabove set forth may be made without departing from the spirit and scope thereof. The specific embodiments are given by way of example only and the invention is limited only by the terms of the appended claims.

What is claimed is:

1. A method for preparing calibration beads for use in calibrating a flow cytometer and for determining the concentration of fluorophore on the calibration beads comprising:

(i) preparing a stable complex consisting of fluorophore and enzyme such that the enzymatic activity is correlated to fluorophore concentration;

(ii) coating a bead with said fluorophore-enzyme complex;

(iii) experimentally measuring the activity of the enzyme in the bead-fluorophore-enzyme complex; and (iv) determining the concentration of fluorophore per bead using the activity of the enzyme determined in (iii).

2. The method of claim 1 wherein the fluorophore is selected from the group consisting of phycoerythrin, APC, Per-CP, and fluoresceinisothiocyanate.

3. The method of claim 1 wherein the enzyme is alkaline phosphatase.

The method of claim 1 wherein the bead is made of polymethylemethacrylate which possesses amino groups on the surface.

4. The method of claim 3 wherein a ratio of the fluorophore to the alkaline phosphatase is 1:1 (mole/mole).

5. The method of claim 1 wherein the bead is made of polymethylemethacrylate which possesses amino groups on the surface.

6. The method of claim 5, wherein the bead is first complexed with biotin and then coated with streptavidin.

7. The method of claim 6, wherein the fluorophore-enzyme complex is biotinylated and then bound to streptavidin coated biotinylated beads.

8. A method for preparing calibration beads for use in calibrating a flow cytometer and for determining the concentration of fluorophore on the calibration beads comprising:

(i) preparing a conjugate of enzyme-fluorophore-biotin such that the enzymatic activity is correlated to fluorophore;

(ii) admixing said conjugate with a streptavidin coated bead to form a bead-streptavidin-biotin-fluorophore-enzyme complex;

(iii) experimentally measuring the activity of the enzyme in the complex; and (iv) determining the concentration of fluorophore in the complex using the activity of the enzyme determined in (iii).

9. The method of claim 8 wherein the fluorophore is selected from the group consisting of phycoerythrin, APC, Per-CP, and fluoresceinisothiocyanate.

10. The method of claim 8 wherein the enzyme is alkaline phosphatase.

11. The method of claim 8 wherein a ratio of fluorophore to alkaline phosphatase is 1:1 (mole/mole).

12. The method of claim 8 wherein the bead is made of polymethylemethacrylate which possesses amino groups on the surface.

13. The method of claim 12, wherein the bead is first complexed with biotin and then coated with streptavidin.

14. The method of claim 13 wherein the fluorophore-enzyme complex is biotinylated and then bound to streptavidin coated biotinylated beads.

* * * * *